United States Patent [19]

Tien et al.

[11] 4,387,359
[45] Jun. 7, 1983

[54] TITANIA OXYGEN SENSOR WITH CHROME OXIDE COMPENSATOR

[75] Inventors: Tseng-Ying Tien, Ann Arbor, Mich.; David C. Weber, Toledo; Philip R. Woodruff, Tiffin, both of Ohio

[73] Assignee: Bendix Autolite Corporation, Fostoria, Ohio

[21] Appl. No.: 226,652

[22] Filed: Jan. 21, 1981

[51] Int. Cl.³ .............................................. H01L 7/00
[52] U.S. Cl. ........................................ 338/34; 422/98
[58] Field of Search ............ 338/34, 28; 73/23, 27 R; 422/58; 23/232 E; 252/518, 520

[56] References Cited

U.S. PATENT DOCUMENTS

| | | | |
|---|---|---|---|
| 3,695,848 | 10/1972 | Taguchi | 23/254 E |
| 3,900,815 | 8/1975 | Taguchi | 338/34 |
| 4,001,756 | 1/1977 | Heijne | 338/34 |
| 4,007,435 | 2/1977 | Tien | 338/34 |
| 4,147,513 | 4/1979 | Bienkowski et al. | 422/98 |
| 4,225,842 | 9/1980 | Schlesselman | 338/34 |

FOREIGN PATENT DOCUMENTS

| | | |
|---|---|---|
| 1512 | 4/1979 | European Pat. Off. |
| 2817873 | 10/1978 | Fed. Rep. of Germany |
| 2005026 | 4/1979 | United Kingdom |

*Primary Examiner*—C. L. Albritton
*Attorney, Agent, or Firm*—Leo H. McCormick, Jr.; Ken C. Decker

[57] ABSTRACT

An oxygen sensor utilizes a chrome oxide compensating resistor (5) in series with a titania sensing resistor (3). The chrome oxide resistor (5) not only compensates for the effects of temperature on the titania sensing (3) resistor, but since it exhibits (p) type behavior while the titania exhibits (n) type behavior in the presence of gaseous oxygen, the sensitivity of the sensor is increased. The resistors (3, 5) can be applied as a film to a substrate (7) or they can be formed as discrete chips. Substantial quantities of alumina and glass can be added to the chrome oxide without affecting oxygen sensitivity although the electrical resistance rises substantially.

12 Claims, 2 Drawing Figures

TITANIA OXYGEN SENSOR WITH CHROME OXIDE COMPENSATOR

This invention relates to an oxygen sensor especially useful in monitoring the oxygen content of internal combustion engine exhaust gases. More particularly, it relates to sensors employing a first resistor having an electrical resistance which varies as a function of the partial pressure of oxygen in the gases to which the sensing element is exposed and a second resistor which compensates for the temperature dependency of the oxygen sensitive resistor. The present invention is directed to a sensor in which chrome oxide is used in the compensating resistor.

It is well known that the electrical resistance of a number of metal oxides varies as a function of the partial pressure of oxygen in a gas mixture to which the metal oxide is exposed. Titanium dioxide (titania) has been widely used as the active element in resistance type oxygen sensors employed to monitor the air/fuel ratio of internal combustion engines. Such sensors operate in step wise fashion to indicate whether the mixture is rich or lean. The signal generated by such a sensor is used to operate the engine so as to increase engine efficiency and to reduce pollution. Unfortunately, the resistivity of the titania resistor varies as a function of temperature as well as the partial pressure of oxygen to which it is exposed. In fact the variation in temperature of the exhaust gases over the operating range of the typical internal combustion engine is so large that ambiguous readings of the oxygen content of the gases would be generated if corrective steps were not taken. Zirconium dioxide has been used successfully as the temperature compensating resistor since its electrical resistance responds to variations in temperature in very much the same manner as titania and it is, for all practical purposes, insensitive to the partial pressure of oxygen to which it is exposed. U.S. Pat. No. 4,147,513 discloses a sensor using titanium dioxide as the active element and zirconium dioxide as the compensating element but it also suggests several other materials for the compensating resistor such as yttrium oxide ($Y_2O_3$); aluminum oxide ($Al_2O_3$), Cerium oxide ($CeO_2$), hafnium oxide ($HfO_2$) and thorium oxide ($Th_2O_3$). In the sensor described in detail, a chip of titania and a second chip of zirconia are mounted in a plug which is inserted into the exhaust stream of an internal combustion engine. The chips are connected through leads extending through the plug to an electrical measuring circuit which generates an output signal indicative of whether the air/fuel ratio of the air/fuel mixture is above or below stiochiometric.

U.S. Pat. No. 4,007,435 discloses a sensor in which the titania and zirconia resistors are in the form of thick films applied to a ceramic substrate as a powder mixed with a liquid vehicle and an organic binder which is then fired to fix the film on the substrate. The ceramic substrate in which an electrical resistance heater is embedded for bringing the sensor rapidly to operating temperature is secured in the exhaust stream of an internal combustion engine by a plug.

U.S. Pat. No. 4,001,756 suggests that an oxygen sensitive metal oxide can be doped to provide a sensor having two measuring elements, one having a p-type conductivity and the other having n-type conductivity. The two elements are pressed to form a sensor in which each element is exposed to the gas to be analysed. With both elements composed of the same oxide, preferably lead oxide, output of the sensor is said to be substantially independent of temperature in a range of 400° to 700° C. Manganese oxide is suggested as another metal oxide which can be doped to have either p or n type conductivity. It is also suggested; however, that the sensor could be made with metal oxides such as titanium dioxide or cerium dioxide, which can only be prepared as n-type semiconductors, serving as one element and a metal oxide, which can only be prepared as a p-type semiconductor, such as nickel oxide or cobalt-oxide as the second element.

SUMMARY OF THE INVENTION

According to the invention, the voltage generated at the common junction (13) of two serially connected resistors, one of which (3) consists essentially of titania and the other chrome oxide (5), varies as a function of the partial pressure of oxygen in an exhaust gas in which the two resistors are immersed essentially independently of the temperature of the exhaust gas. In such a sensor, the electrical resistance of the titania varies directly with the partial pressure of oxygen while the electrical resistance of the chrome oxide has an inverse relation thereto. At the same time, the electrical resistance of both materials, decreases at substantially the same rate with increasing temperature. The complementary response of the titania and the chrome oxide to the partial pressure of oxygen results in a sensor which is particularly sensitive, and the similar response of the materials to the temperature of the gas permits the sensor to operate over a wide temperature range such as that found in a typical internal combustion engine.

The resistors (3, 5) can be applied as a film to a substrate or they can be formed as discrete chips. Suitable films forming the second resistor (5) can be made from an ink having a composition ranging from 60% calcined chrome oxide, 30% fritted platinum paste and 10% glass to 90% calcined chrome oxide and 10% fritted platinum paste. Such a mixture can be fired at the relatively low temperature of 850° C. which is considerably less than that required to fire the previously used zirconia film.

It has been found that the addition of alumina to the chrome oxide ink does not affect the sensitivity of the chrome oxide resistor (5) to the partial pressure of oxygen; however, it does raise the resistivity of the resultant film. Considerable success has been achieved making thick film sensors using 65% chrome oxide and 35% alumina ink for the second resistor (5) and 80% titania and 20% platinum for the first resistor (3). The films are of equal area and good compensation is attained at both 340° and 800° C.

Suitable chrome oxide films were also produced by adding up to 60% by weight of glass to the chrome oxide. In addition, a calcine of 50% chrome oxide and 50% zirconia was used in an ink comprised of 80% of the calcine, 10% glass and 10% platinum to produce another suitable film.

Discrete chrome oxide resistor chips can be made from cast tapes. In this process, calcined and milled chrome oxide is blended with glass, a binder, plasticizer and solvents and cast on an acetate film. Preferably, the calcine is made of from 65–79% chrome oxide and 35–21% alumina. The glass is added to the calcine to give the resultant chip the desired electrical resistance and strength.

DESCRIPTION OF THE PREFERRED EMBODIMENTS

Figure 1:
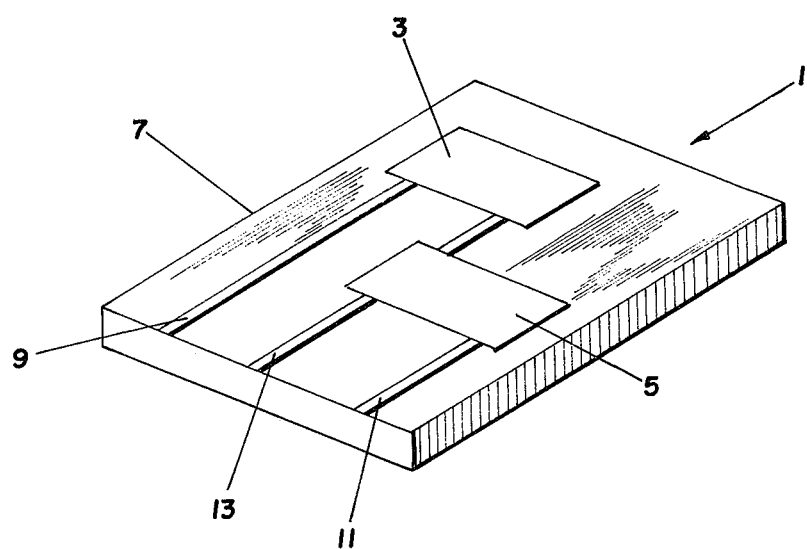
FIG. 1 is a schematic diagram of a sensor made in accordance with the teachings of the invention.

As shown in FIG. 1, the oxygen sensor 1 of the present invention may be in the form of thick films 3 and 5 of resistive material forming two resistors applied to a substrate 7. The first resistor 3, which is referred to as the sensor element, consists essentially of titania. The electrical resistivity of this resistor is partically sensitive to the partial pressure of oxygen to which the resistor is exposed. Since its electrical resistance also varies as a function of temperature, a second resistor 5 known as the copensator resistor is also provided. In accordance with the teachings of this invention, this resistor consists essentially of chrome oxide. The primary purpose of the second resistor 5 is to compensate for the changes in the temperature of the gases to which the sensor is exposed. However, the electrical resistances of this chrome oxide resistor also varies as a function of partial pressure of oxygen to which it is exposed but in the opposite sense from that of the titania resistor 3. The titania resistor 3 exhibits (n) type electrical behavior in the presence of gaseous oxygen: that is its electrical resistance increases as the partial pressure of oxygen increases. The chrome oxide resistor 5, on the other hand, exhibits (p) type electrical behavior under similar conditions and its electrical resistivity decreases with increases in the partial pressure of oxygen.

The complementary response of the titania and chrome oxide resistors to the presence of gaseous oxygen can be used to advantage in providing a more sensitive oxygen sensor. As shown in FIG. 1, the resistor films 3 and 5 are connected in series between leads 9 and 11 by a lead 13 forming the common junction between the resistor films. Thus by applying a reference voltage across the leads 9 and 11 the voltage at the common junction 13 is an indication of the partial pressure of oxygen to which the sensor is exposed. Since the electrical resistance of the titania resistor film 3 goes up in presence of high levels of gaseous oxygen and the resistance of the chrome oxide resistor goes down under these conditions, and since the reverse of these conditions occurs for low levels of oxygen, the voltage changes at lead 13 for the subject sensor are much more sensitive to the partial pressure of oxygen than the prior art sensors using zirconia for the second resistor. Since the titania and chrome oxide resistors have a similar response to changes in temperature, the voltage at the common junction 13 is insensitive to changes in temperature of the sensed gas.

The subject sensor is particularly adapted for use in detecting the air/fuel ratio of air/fuel mixtures for internal combustion engines. In such an environment, the sensor will generate one voltage at the lead 13 when the mixture is lean and another discrete voltage when the mixture is rich. The sensor may be utilized with the circuitry disclosed in U.S. Pat. No. 4,147,513 which is hereby incorporated by reference into this specification for the purpose of illustrating a complete system for detecting the air/fuel ratio of the fuel mixture of an internal combustion engine.

The chrome oxide resistor 5 of this invention can be in the form of a thick film as shown in FIG. 1 or can be a discrete chip such as the compensator resistor in U.S. Pat. No. 4,147,513. In the case of the thick film, the ink applied to the substrate can have a composition ranging from 60% calcined chrome oxide, 30% fritted platinum paste and 10% glass to 90% calcined chrome oxide and 10% fritted platinum paste. These compositions are mixed with an organic vehicle, such as toulene-pine oil so that the ink can be applied by painting, screen printing, and/or pad printing on the substrate. After printing and drying, the chrome oxide ink is matured by firing in air to a temperature of 850° C. for one-half hour. The relatively low firing temperature of the ink is made possible by the platinum paste addition.

The resulting matured, unstabilized chrome oxide resistor will exhibit (p) type behavior when switched from rich to lean or vice versa on a functional test burner at elevated temperatures. For equivalent resistor geometries and temperatures, between 450° C. and 850° C., the rich and lean resistance values of the chrome oxide resistor lie between the rich and lean resistance values of the titania sensor resistor 3.

Some work has been done on the effects of various additions to the chrome oxide ink composition. The purpose of these studies was to determine if the resistivity and/or the (p) type behavior of pure chrome oxide could be altered by these additions. The additions studied were alumina, zirconia and glass.

Table I below illustrates the resistivity values for pure chrome oxide thick films. The ink in this example consisted of 90% calcined pure chrome oxide and 10% glass.

TABLE I

| PIECE NO. | TEST TEMPERATURE | RESISTIVITY RICH | LEAN |
|---|---|---|---|
| 1 | 392° C. | 16,000 | 67 |
| 2 | 392° C. | 14,000 | 50 |
| 3 | 392° C. | 20,000 | 60 |
| 1 | 500° C. | 1,700 | 29 |
| 2 | 500° C. | 1,000 | 23 |
| 3 | 500° C. | 2,000 | 26 |
| 1 | 600° C. | 266 | 19 |
| 2 | 600° C. | 130 | 16 |
| 3 | 600° C. | 316 | 21 |
| 1 | 800° C. | 46 | 16 |
| 2 | 800° C. | 36 | 15 |
| 3 | 800° C. | 45 | 15 |
| 90% Calcine (100% $Cr_2O_3$) | | | |
| 10% glass (KD843A Ferro) | | | |

Condiderable work has been done on analyzing the effects of alumina additions to the chrome oxide. Tables II and III below illustrate the resistivity values for chrome oxide thick films made from 22% and 35% weight percent alumina additions respectively.

TABLE II

| PIECE NO. | TEST TEMPERATURE | RESISTIVITY RICH | LEAN |
|---|---|---|---|
| 1 | 393° C. | 1,000,000 | 2,500 |
| 2 | 393° C. | 1,000,000 | 10,000 |
| 3 | 393° C. | 1,000,000 | 130,000 |
| 4 | 393° C. | 1,000,000 | 17,000 |
| 5 | 393° C. | 1,000,000 | 5,000 |
| 1 | 500° C. | 200,000 | 500 |
| 2 | 500° C. | 320,000 | 2,000 |
| 3 | 500° C. | 300,000 | 17,000 |
| 4 | 500° C. | 190,000 | 1,200 |
| 5 | 500° C. | 200,000 | 2,000 |
| 1 | 600° C. | 60,000 | 240 |

TABLE II-continued

| PIECE NO. | TEST TEMPERATURE | RESISTIVITY RICH | LEAN |
|---|---|---|---|
| 2 | 600° C. | 60,000 | 800 |
| 3 | 600° C. | 65,000 | 10,400 |
| 4 | 600° C. | 100,000 | 700 |
| 5 | 600° C. | 60,000 | 1,000 |
| 1 | 800° C. | 6,000 | 200 |
| 2 | 800° C. | 7,000 | 340 |
| 3 | 800° C. | 13,000 | 1,300 |
| 4 | 800° C. | 6,000 | 300 |
| 5 | 800° C. | 4,000 | 400 |

90% Calcine (78% $Cr_2O_3$ - 22% $Al_2O_3$)
10% Glass (KD 843A Ferro)

TABLE III

| PIECE NO. | TEST TEMPERATURE | RESISTIVITY RICH | LEAN |
|---|---|---|---|
| 1 | 395° C. | 11,000,000+ | 3,700 |
| 2 | 395° C. | 11,000,000+ | 36,000 |
| 3 | 395° C. | 11,000,000+ | 23,000 |
| 4 | 395° C. | 11,000,000+ | 14,000 |
| 1 | 500° C. | 1,100,000 | 1,300 |
| 2 | 500° C. | 1,100,000 | 5,000 |
| 3 | 500° C. | 1,100,000 | 6,000 |
| 4 | 500° C. | 1,100,000 | 3,500 |
| 1 | 600° C. | 77,000 | 600 |
| 2 | 600° C. | 370,000 | 2,000 |
| 3 | 600° C. | 560,000 | 2,000 |
| 4 | 600° C. | 230,000 | 1,500 |
| 1 | 800° C. | 2,700 | 150 |
| 2 | 800° C. | 13,000 | 400 |
| 3 | 800° C. | 19,000 | 440 |
| 4 | 800° C. | 14,400 | 440 |

85% Calcine (65% $Cr_2O_3$ - 35% $Al_2O_3$)
5% Platinum Paste (LP11 - 4495, Plessy)
10% Glass (KD 843A, Ferro)

Comparing the data of Tables I, II and III reveals that the increasing alumina additions do not alter the (p) type behavior of the resistor significantly. The lean and rich resistivity values, particularly the rich, increase with increasing alumina content.

Considerable success has been achieved making thick film sensors using the 65% chrome oxide—35% alumina ink for the compensator resistor 5 and 80% titania—20% platinum for the sensor resistor 3. These sensors are of equal area and good compensation is attained at both 340° C. and 800° C. Results obtained from several sensors made with these inks are shown in Table IV. This table shows not only the output voltages generated for rich and lean mixtures at 392° C. and 800° C., but also the time reuired in milli seconds to switch from rich to lean and vice versa ("response (MS)") and a comparison of the response of these resistors as compared to a zirconia sensor ("lag (MS)"). This lag measurement indicates the difference between the time for the titania-chrome oxide thick film sensor to generate a 500 mv. output and the time for the zirconia sensor to generate a 400 mv. output upon switching. The zirconia sensor used in the comparison is of the type known as a solid electrolyte thimble in which an emf is generated when a difference in the partial pressure of oxygen exists between the inside and outside of the thimble.

TABLE IV

| SEN-SOR No. | OUTPUT (mv) RICH | LEAN | RESPONSE (ms) R → L | L → R | LAG (ms) R-L | L-R | TEMP. °C. |
|---|---|---|---|---|---|---|---|
| 1 | .997 | .178 | 33 | 11 | −3.0 | 37.0 | 392 |
| 2 | 1.000 | .013 | 14 | 8 | 18.0 | 20.0 | 392 |
| 3 | 1.000 | .070 | 31 | 21 | 52.0 | 39.0 | 392 |
| 4 | 1.000 | .085 | 30 | 27 | 66.0 | 19.0 | 392 |
| 5 | 1.000 | .113 | 91 | 23 | 62.0 | 42.0 | 392 |
| 1 | .985 | .068 | 25.0 | 13 | 22 | 37 | 800 |
| 2 | .994 | .056 | 12 | 9 | 8 | 10 | 800 |
| 3 | .992 | .145 | 26 | 16 | 29 | 19 | 800 |
| 4 | .994 | .112 | 18 | 16 | 23 | 2 | 800 |
| 5 | .993 | .076 | 68 | 14 | 22 | 32 | 800 |

The effect of glass additions is shown in Table V.

TABLE V

| Sample No. | Test Temp. | RESISTANCE VALUES Chrome Oxide Rich | Lean | Sensor Material Rich | Lean |
|---|---|---|---|---|---|
| I. 60% Chrome Oxide, 30% Platinum Paste, 10% Glass | | | | | |
| 1 | 450° C. | 300,000 | 20,000 | 2,000 | 5,000,000 |
| 2 | 450° C. | 150,000 | 12,000 | 2,000 | 10,000,000 |
| 3 | 450° C. | 130,000 | 7,000 | 4,000 | 5,000,000 |
| 1 | 800° C. | 1,400 | 430 | 60 | 10,300 |
| 2 | 800° C. | 1,400 | 400 | 20 | 4,000 |
| 3 | 800° C. | 600 | 200 | 80 | 20,000 |
| II. 40% Chrome Oxide, 60% Glass | | | | | |
| 1 | 450° C. | 3,600,000 | 350,000 | 8,000 | 7,000,000 |
| 1 | 800° C. | 200 | 580 | 220 | 18,000 |
| III. 65% Chrome Oxide, 35% Glass | | | | | |
| 1 | 450° C. | 5,000,000 | 480,000 | 8,000 | 7,000,000 |
| 1 | 800° C. | 2,800 | 1,000 | 130 | 45,000 |
| IV. 80% Calcine (50 $ZrO_2$ - 50 $Cr_2O_3$), 10% Pt Paste, 10% Glass | | | | | |
| 1 | 450° C. | 20,000,000+ | 800,000 | 10,000 | 20,000,000 |
| 1 | 800° C. | 42,000 | 21,000 | 100 | 38,000 |

This table shows that glass additions do not diminish the (p) type behavior until the glass content is 60% by weight. Even at this glass loading, the influence of the glass occurs only at 800° C. test temperature. The table does show that as the glass content is increased from 10 to 60%, the resistance values increase tenfold. The resistance values for the inks containing 10–60% glass lie between the rich and lean resistance values of an equivalent sized titania sensor element.

A small reduction in (p) type behavior and an increase in resistance can be obtained if the calcined material used in the ink formulation is a combination of chrome oxide and zirconia. The calcine is made by mixing 50% chrome oxide and 50 % zirconia and firing at 2800° F. for 18 hours. A typical ink composition for use with this calcine is 80% calcine, 10% glass, and 10% platinum paste.

Discrete chrome oxide resistor chips can be made from chrome oxide cast tapes. In the tape process, calcined and milled chrome oxide is blended with a binder, such a polyvinyl butyrl, a plasticizer and solvents and cast on an acetate film using a doctor blade. The preferred slip viscosity for casting is approximately 1700 cps. After air drying the tape for 12 hours, small sized shapes are punched or cut out. The shape is placed, acetate backing down, in a fixture and precut platinum wires are placed and held in position by the fixture. The surface of the shape is wetted with a drop of acetone and a second shape, acetate backing up, is placed on top to sandwich the wire leads. The acetone reactivates the binder and causes the pieces to stick together. The assembly is then compressed to the desired thickness, and heated gently to approximately 75° C. The backing material (acetate) can then be gently peeled away. This assembly is heated slowly under vacuum to drive off the volatile species and finally fired at 1200° C. to consolidate the ceramic powder.

A typical tape composition for the chrome oxide chip is as follows:

TABLE VI

| polyvinyl butyrl | 6.2% |
|---|---|
| plasticizer | 7.3% |
| solvent (blend) | 41.0% |
| calcine (100% $Cr_2O_3$) | 43.0% |
| glass frit | 2.3% |
| wetting agent | 0.2% |

The chips made from this tape obtain the desired resistance and strength properties when fired in air to around 2300° F. for 1 hour. Preferred compositions contain a combination calcined, milled chrome oxide and alumina and glass in place of 100% calcined chrome oxide. The chrome oxide-alumina calcine is made in a preliminary process by calcining 65–79% chrome oxide and 21–35% alumina at 2900° F. for 40 hours. The calcined chrome oxide-alumina is then wet milled, dried and ready for tape casting. The glass addition to the tape is made so that the resultant chip can obtain the desired resistance and strength properties by firing at 2300° F. for one hour. Two preferred compositions appear in TAble VII.

TABLE VII

| Polyvinyl butyrl | 6.2% | | 6.2% |
|---|---|---|---|
| Plasticizer | 7.3% | | 7.3% |
| Solvent | 41.0% | | 41.0% |
| Calcine (79$Cr_2O_3$ - 21$Al_2O_3$) | 43.0% | (65$Cr_2O_3$ - 35$Al_2O_3$) 43.0% | |
| Glass | 2.3% | | 2.3% |
| Wetting Agent | 0.20% | | 0.2% |

Figure 2:
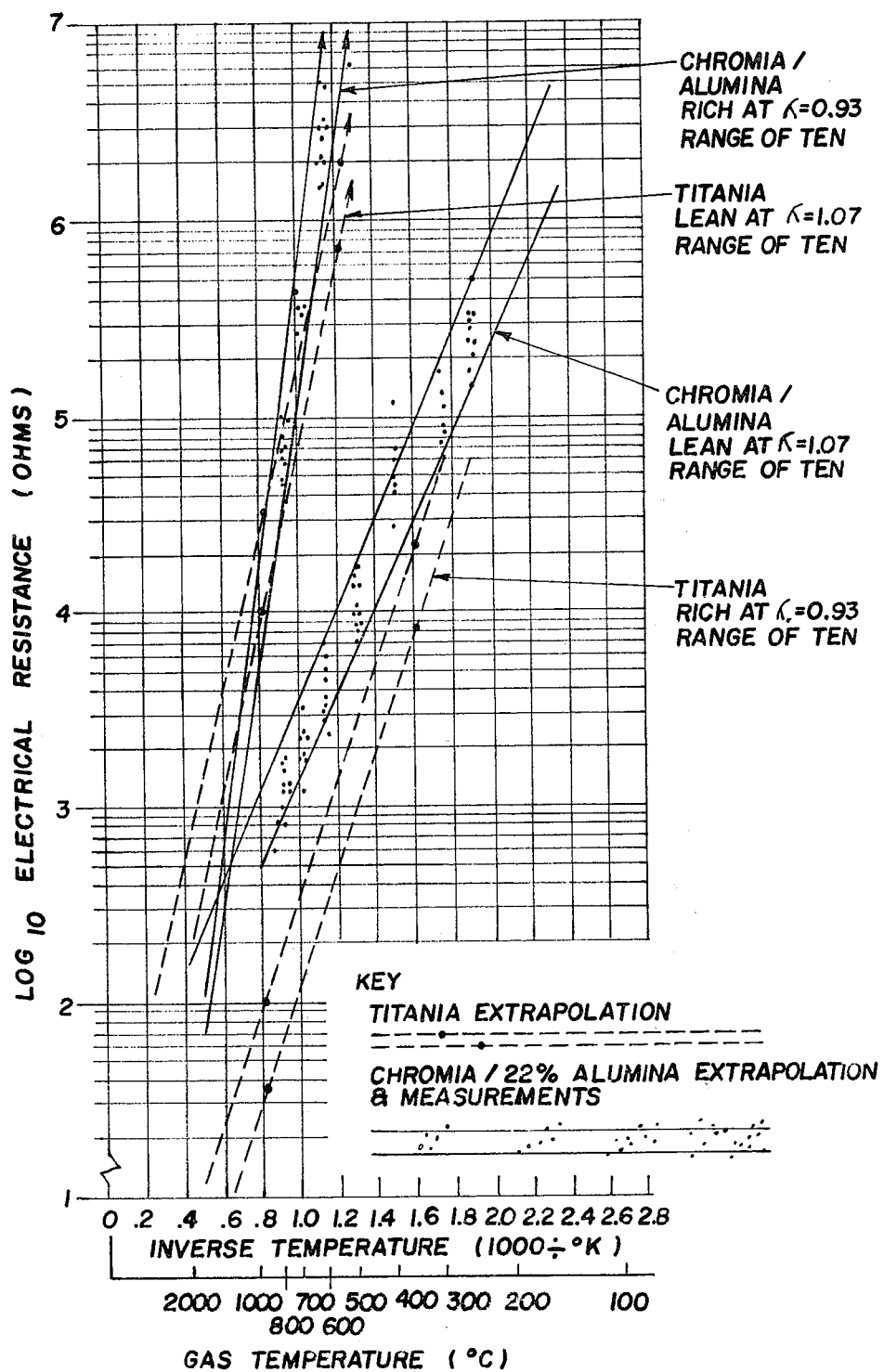
FIG. 2 is a logarithmic chart illustrating the response of a sensor made in accordance with the invention.

The fired chips made from the compositions set forth in Table VII have good strength and exhibit (p) type behavior when switched from rich to lean or vice versa on a functional test burner at both 390° and 850° C. gas stream temperatures. For equivalent chip geometries and temperatures between 250° C. and 800° C., the chrome-alumina glass chip nearly perfectly compensates the titania sensor chip. A plot of log resistance versus temperature for such a chip is shown in FIG. 2.

While the invention is disclosed in what is conceived to be practical and effective embodiments, it is recognized that departures can be made therefrom which are fully within the spirit of the invention. Accordingly, the invention is not to be limited to the details specifically disclosed but is to be accorded the full scope of the appended claims, including any and all equivalents thereof.

We claim:

1. A titania oxygen sensor with a chrome oxide compensator for detecting the oxygen content in an exhaust gas, said sensor comprising a first resistor comprised of titania, the resistance of which varies as a function of both the temperature of the exhaust gas to which it is exposed and the partial pressure of oxygen in the exhaust gas, and a second resistor consisting essentially of a calcine of chromium oxide and a modifier selected from a group consisting of aluminum oxide, zirconium oxide, platinum and glass, the resistance of which varies as a function of temperature in the same sense as the titania but varies as a function of the partial pressure of oxygen in the exhaust gas in the opposite sense to that of the titania, said first and second resistors being connected in series with a common junction such that with a source voltage connected across the two series connected resistors the voltage generated at said common junction is a function of the partial pressure of the exhaust gas to which the two resistors are exposed despite variations in the temperature of the exhaust gases.

2. The oxygen sensor of claim 1 wherein said first resistor comprises about 80% by weight titanium oxide and 20% platinum, the second resistor comprises a calcine of 65% by weight chromium oxide and 35% aluminum oxide, and wherein said first and second resistors are applied as a film to substantially equal areas on a substrate.

3. The oxygen sensor of claim 1 wherein said calcined and chromium oxide consists essentially of 65–79% by weight chromium oxide and 21–35% aluminum oxide.

4. The oxygen sensor of claim 1 wherein said second resistor consists essentially of a calcine of chromium oxide and up to about 35% by weight aluminum oxide.

5. The oxygen sensor of claim 1 wherein said second resistor comprises about 60% to 90% by weight of said calcine and from about 30% to 10% by weight of glass.

6. The oxygen sensor of claim 1 wherein said second resistor consists of a calcine of chromium oxide and up to about 10% by weight of glass.

7. The oxygen sensor of claims 5 wherein the ingredients in said first and second resistors are mixed with an organic vehicle and the resultant mixture is applied to a substrate, dried and fired in air to a temperature of about 850° C. for about one-half hour.

8. The sensor of claim 1 wherein said second resistor consists essentially of a calcine of chromium oxide and up to 60% glass.

9. The oxygen sensor of claim 1 wherein said second resistor consists essentially of a calcine of 50% by weight chromium oxide and 50% by weight of zirconium oxide.

10. The oxygen sensor of claim 1 wherein said second resistor comprises about 80% by weight of said calcine, 10% by weight of glass and 10% by weight of platinum, said platinum being in the form of a paste.

11. The oxygen sensor of claim 1 wherein said second resistor further includes a binder, plasticizer and a solvent which are combined with said chrome oxide and selected modifier to form a mixture which is applied to a tape, said tape being cut into desired shapes, several pieces of said tape being laminated together and electrical leads being connected to said second resistor and fired at a temperature of about 2300° F. to produce a unitray structure.

12. The oxygen sensor of claim 6 wherein the ingredients in said first and second resistors are mixed with an organic vehicle and the resultant mixture is applied to a substrate, dried and fired in air to a temperature of about 850° C. for about one-half hour.

* * * * *